United States Patent
Chuang et al.

(10) Patent No.: US 9,494,531 B2
(45) Date of Patent: Nov. 15, 2016

(54) MULTI-SPOT ILLUMINATION FOR IMPROVED DETECTION SENSITIVITY

(71) Applicant: KLA-Tencor Corporation, Milpitas, CA (US)

(72) Inventors: Yung-Ho Alex Chuang, Cupertino, CA (US); Xiaoxu Lu, San Jose, CA (US); John Fielden, Los Altos, CA (US); Ivan Maleev, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/455,161

(22) Filed: Aug. 8, 2014

(65) Prior Publication Data
US 2015/0041666 A1 Feb. 12, 2015

Related U.S. Application Data

(60) Provisional application No. 61/864,024, filed on Aug. 9, 2013.

(51) Int. Cl.
| | |
|---|---|
| *G01N 21/88* | (2006.01) |
| *G01J 1/04* | (2006.01) |
| *G01N 21/95* | (2006.01) |

(52) U.S. Cl.
CPC ........... *G01N 21/9501* (2013.01); *G01J 1/04* (2013.01); *G01N 21/8806* (2013.01)

(58) Field of Classification Search
CPC .............. G01N 21/9501; G01N 21/8806; G01J 1/04
See application file for complete search history.

(56) References Cited

U.S. PATENT DOCUMENTS

| | | | |
|---|---|---|---|
| 3,904,267 A | 9/1975 | de Veer | |
| 4,870,268 A * | 9/1989 | Vincent | G02B 27/1006 250/226 |

(Continued)

FOREIGN PATENT DOCUMENTS

| | | |
|---|---|---|
| EP | 2401599 A1 | 9/2010 |
| EP | 2012313 B1 | 10/2012 |

(Continued)

OTHER PUBLICATIONS

International Search Report and Written Opinion mailed on Nov. 24, 2014, for PCT Application No. PCT/US2014/050395 filed on Aug. 8, 2014, by KLA-Tencor Corporation, 9 pages.

*Primary Examiner* — Yara B Green
(74) *Attorney, Agent, or Firm* — Spano Law Group; Joseph S. Spano

(57) ABSTRACT

Methods and systems for minimizing interference among multiple illumination beams generated from a non-uniform illumination source to provide an effectively uniform illumination profile over the field of view of an inspection system are presented. In some examples, a pulsed beam of light is split into multiple illumination beams such that each of the beams are temporally separated at the surface of the specimen under inspection. In some examples, multiple illumination beams generated from a non-uniform illumination source are projected onto spatially separated areas on the surface of the specimen. A point object of interest illuminated by each area is imaged onto the surface of a time-delay integration (TDI) detector. The images are integrated such that the relative position of the illumination areas along the direction of motion of the point object of interest has no impact on the illumination efficiency distribution over the field of view.

19 Claims, 12 Drawing Sheets

(56) References Cited

U.S. PATENT DOCUMENTS

| | | |
|---|---|---|
| 5,844,727 A | 12/1998 | Partlo |
| 6,181,421 B1 | 1/2001 | Aspnes et al. |
| 6,201,601 B1 | 3/2001 | Vaez-Iravani |
| 6,275,514 B1 | 8/2001 | Katzir et al. |
| 6,278,519 B1 | 8/2001 | Rosencwaig et al. |
| 6,567,584 B2 | 5/2003 | Carlisle et al. |
| 6,606,173 B2 | 8/2003 | Kappel et al. |
| 6,801,368 B2 | 10/2004 | Coufal et al. |
| 6,909,854 B1 | 6/2005 | Kleiner et al. |
| 7,193,710 B1 | 3/2007 | Johs et al. |
| 7,400,457 B1 | 7/2008 | Cayer |
| 7,525,649 B1 | 4/2009 | Leong et al. |
| 7,548,370 B2 | 6/2009 | Albert et al. |
| 7,843,653 B2 | 11/2010 | Cayer |
| 7,916,391 B2 | 3/2011 | Albert et al. |
| 7,969,543 B2 | 6/2011 | Kwok et al. |
| 8,049,866 B2 | 11/2011 | McCarthy |
| 8,120,848 B2 | 2/2012 | Isano |
| 8,212,995 B2 | 7/2012 | Koehler et al. |
| 8,502,979 B2 | 8/2013 | Levy et al. |
| 2003/0227618 A1* | 12/2003 | Some .................. G01N 21/9501 356/237.1 |
| 2004/0001255 A1 | 1/2004 | Fratello |
| 2004/0175028 A1* | 9/2004 | Cavan ................... G06T 3/4069 382/145 |
| 2009/0219491 A1 | 9/2009 | Williams et al. |
| 2010/0188762 A1 | 7/2010 | Cook |
| 2011/0085221 A1 | 4/2011 | Ortyn et al. |
| 2013/0016346 A1 | 1/2013 | Romanovsky et al. |
| 2013/0077070 A1 | 3/2013 | Schimmel et al. |
| 2013/0077076 A1 | 3/2013 | Patra et al. |
| 2013/0271741 A1 | 10/2013 | Saenger |

FOREIGN PATENT DOCUMENTS

| | | |
|---|---|---|
| KR | 1020090117691 A1 | 11/2009 |
| WO | 2008091290 | 7/2008 |
| WO | 2010099118 A1 | 9/2010 |
| WO | 2012102603 A1 | 8/2012 |
| WO | 2013009550 A2 | 1/2013 |

* cited by examiner

MULTI-SPOT ILLUMINATION FOR IMPROVED DETECTION SENSITIVITY

CROSS REFERENCE TO RELATED APPLICATION

The present application for patent claims priority under 35 U.S.C. §119 from U.S. provisional patent application Ser. No. 61/864,024, entitled "Split Gaussian Beams and Multi-Spot Flat-Top Illumination for Surface Scanning Systems," filed Aug. 9, 2013, the subject matter of which is incorporated herein by reference.

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. Various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on both unpatterned and patterned wafer surfaces while maintaining high throughput. Similarly, inspection systems are required to capture a wider range of physical defects on reticle surfaces.

One such inspection system is a scanning surface inspection system that illuminates and inspects a wafer surface. The wafer is scanned under an illumination spot until the desired portion of the wafer surface is inspected. Typically, a high-power, laser based illumination source generates illumination light with a non-uniform (e.g., Gaussian) beam intensity profile. However, it is generally desirable to project illumination light onto the specimen under inspection with an intensity distribution that is as uniform as possible over the field of view of the inspection system.

For example, in high-power, laser-based inspection systems, the power density of the incident laser beam is capable of damaging the wafer surface. For inspection systems employing a short-pulsed laser illumination source, substrate damage is primarily related to peak power density. An excessive amount of heat is generated by the interaction of the incident optical radiation with the wafer surface, particularly in areas of incidence subject to incident light with peak power density.

In another example, imaging systems generally rely on illumination light having an intensity distribution that is as uniform as possible over the field of view to effectively image the surface of the specimen.

One approach to generating a uniform intensity distribution from a non-uniform (e.g. Gaussian) beam source is to use only the center portion of the beam profile. While robust and simple, a significant amount of light is wasted; at significant system cost. In addition, care must be taken to properly dump the unused light while avoiding stray light issues.

Another approach involves the use of a diffractive optical element (DOE) that receives the non-uniform input beam and generates multiple secondary beams. By controlling the relative phase and position of the secondary beams, a DOE may generate a composite illumination light that approximates a uniform intensity distribution at the wafer surface.

Unfortunately, DOE elements are highly sensitive to periodic phase and intensity fluctuations in the illumination beam profile (wave front errors), and also to position of input beam with respect to DOE. Furthermore, a manufactured DOE is a fixed optical structure that typically cannot be adapted to accommodate changes in requirements for the final illumination profile. Similarly, a manufactured DOE cannot be actively altered to respond to changes in phase or intensity distribution of an input beam. In addition, DOEs are also relatively expensive both to design and manufacture compared to standard optical components, such as spherical lenses and flat mirrors.

Another approach to generating a uniform distribution involves the use of diffusers. However, diffusers share many of the same problems described hereinbefore with respect to DOEs. In addition, in applications involving coherent illumination, diffusers may give rise to undesired speckle.

Another approach to generating a uniform distribution involves the use aspheric optics. However, aspheric optics share many of the same problems described hereinbefore with respect to DOEs.

In some examples, multiple, independent light sources may be employed to generate a uniform distribution. However, the additional system cost is undesirable.

In general, the disadvantages of existing beam forming systems include low efficiency, sensitivity to aberrations, complexity, and poor flexibility. Typically, systems for generating a uniform distribution from a single Gaussian beam without light dumping are designed to break the input beam into multiple copies, and manipulate each copy individually. Such manipulations include attenuation, phase delay, or repositioning in space. However, such manipulations are significantly impacted by interference between the copies, particularly when real-world aberrations of the input beam are taken into account.

Hence, improvements to scanning inspection systems are desired to mitigate interferences among multiple illumination beams employed to illuminate a specimen under inspection.

SUMMARY

Methods and systems for minimizing interference among multiple illumination beams generated from a non-uniform illumination source to provide an effectively uniform illumination profile over the field of view of an inspection system are presented.

In one aspect, interferences among the multiple illumination beams are effectively mitigated by employing an optical subsystem that generates multiple illumination beams from a pulsed illumination source having a non-uniform intensity distribution. The optical subsystem introduces optical delay among the multiple illumination beams at the surface of the specimen under inspection. Since the multiple beams illuminating the surface are temporally separated, interference among the illumination beams at the detector is minimized.

In another aspect, interferences among the multiple illumination beams are effectively mitigated by employing a time-delay integration (TDI) detector and an optical subsystem that generates multiple illumination beams from an illumination source having a non-uniform intensity distribution. The optical subsystem directs each of the multiple illumination beams to the surface of the specimen under inspection such that each area of the surface of the specimen illuminated by each beam is spatially separate from the others. The TDI detector receives an amount of light collected from each area of the specimen illuminated by each of the illumination beams. A point object imaged by the optical system onto the TDI detector moves across the detector surface with the same speed as the speed of transfer of charges through the detector. Since each illumination area is spatially separated, the point object of interest moves through any illumination areas in the path of the motion trajectory of the point object without interference. The image of the point object illuminated by each illumination area in its path moves across the TDI detector as the associated charge coupled device (CCD) charges are transferred across the detector. Thus, the point object of interest will interact with illumination light from each illumination spot in its motion trajectory and the interaction will be passed to the TDI detector, and integrated. In this manner, the relative position of the illumination spots along the direction of motion of the point object of interest has no impact on the illumination efficiency distribution over the field of view.

Several embodiments of optical subsystems configured to generate multiple illumination beams from an illumination source having a non-uniform intensity distribution are presented by way of non-limiting example. The embodiments presented generate multiple illumination beams at the surface of the specimen under inspection such that each area of the surface of the specimen illuminated by each beam is temporally delayed from at least one of the others, spatially displaced from at least one of the others, or both.

In some embodiments, an optical subsystem is employed to generate copies of a non-uniform illumination beam having approximately equal intensity. In some examples, these copies are directed to the surface of a specimen under inspection with optical delay among the multiple illumination beams. In some examples, the copies are directed to the surface of the specimen under inspection such that the areas of the specimen surface illuminated by each beam are spatially separated. In some examples, the copies are directed to the surface of the specimen under inspection with optical delay among the multiple illumination beams and with spatial separation.

In some embodiments, an optical subsystem is employed to spatially split a non-uniform illumination beam into at least two half-beams. In some examples, a pulsed illumination beam is spatially split into at least two half-beams and any spatially overlapping half-beams are delayed in time longer than the pulse length to avoid interference. In these examples, the half-beams are spatially displaced slightly so that the total intensity profile has a flat top around the center. In some examples, this results in a more effective use of illumination light. In addition, the peak intensity of each pulse is reduced and the lifetime of optics and sensors is improved.

In some embodiments, an illumination beam is incident on a parallel beam plate at a nonzero incident angle and is split into two halves from the center. One part of the beam is directly reflected from the front surface of the plate and the other part of the beam passes through the front surface and is reflected from the back surface. A portion of the reflected beam from the back surface passes through the front surface and another portion is again reflected from the front surface. The added path length creates a spatial shift and also a time delay between any two overlapping beams. Because of the time delay, there is no interference between the beams and the intensity profile integrated within an appropriate period is approximately equal to the sum of the individual intensity profiles.

In some embodiments, an illumination beam is incident on a parallel beam plate that spatially splits the incoming beam and generates two output channels each having an effectively uniform distribution. An incoming beam is incident on the parallel beam plate at a nonzero incident angle and is split into two halves from the center. One half-beam is 50% reflected from the front surface of the plate and the other 50% passes through both front and back surfaces. The other half-beam passes through the front surface and is reflected from the back surface. Subsequently, 50% of the intensity of this half-beam is transmitted through the front surface and the other 50% is again reflected from the front surface and is transmitted through the back surface. The path length differences among the half-beams create a spatial shift and also time delay between the beams.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

In one aspect, interferences among the multiple illumination beams are effectively mitigated by employing an optical subsystem that generates multiple illumination beams from a pulsed illumination source having a non-uniform intensity distribution. The optical subsystem introduces an optical delay among the multiple illumination beams at the surface of the specimen under inspection. Since the multiple beams illuminating the surface are temporally separated, interference among the illumination beams at the detector is minimized.

Figure 1:
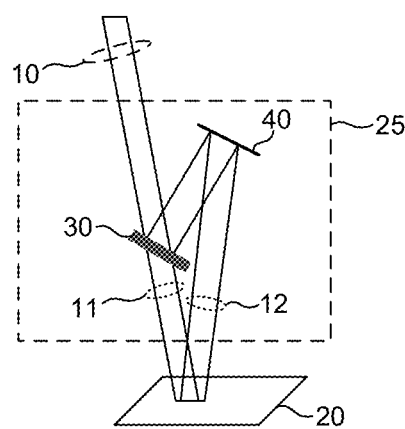
FIG. 1 is a simplified diagram illustrative of an embodiment of an optical subsystem configured to split a beam of incoming illumination light into secondary beams of illumination light that are temporally separated at the surface of the specimen under inspection.

FIG. 1 depicts an embodiment of an optical subsystem 25 configured to split a beam of incoming illumination light into secondary beams of illumination light that are temporally separated at the surface of the specimen under inspection. Optical subsystem 25 receives an amount of illumination light 10 generated by a pulsed illumination source (not shown). The illumination source may include, by way of non-limiting example, a mode-locked or Q-switched laser. In general, the illumination subsystem is configured to direct light having a relatively narrow wavelength band to the optical subsystem 25. The intensity distribution of illumination light 10 is non-uniform. Typically, the intensity distribution of illumination light 10 generated by a laser illumination system is approximated as a Gaussian distribution. As depicted in FIG. 1, optical subsystem 25 includes a beamsplitter 30 that passes a portion 11 of the illumination light 10 and reflects the remaining illumination light 12 toward a mirror element 40. Mirror element 40 redirects illumination light 12 toward the specimen 20 under inspection. In high numerical aperture (NA) illumination systems, mirror 40 may be curved, or complemented with one or more lens elements of sufficient optical power mirror to bring both beams into focus in the same plane. As depicted in FIG. 1, the path lengths of illumination beams 11 and 12 to the surface of specimen 20 are different. Thus, an optical delay is introduced between illumination beams 11 and 12 at the surface of specimen 20.

A detector (not shown) receives an amount of light collected from the surface of specimen 20 illuminated by illumination beam 11, and then a short time later receives another amount of light collected from the surface of specimen 20 illuminated by illumination beam 12. Because of the temporal separation between the two instances of collected light, interference is minimized. Thus, even if the areas of specimen 20 illuminated by illumination beam 11 and 12 spatially overlap, the beams do not interfere.

Figure 2:
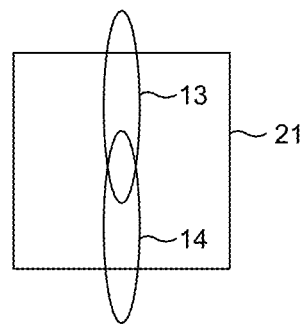
FIG. 2 is a simplified diagram illustrative of a portion of a specimen illuminated by the optical subsystem illustrated in FIG. 1.

FIG. 2 illustrates a portion 21 of the surface of specimen 20 within the field of view of the detector. Area 13 is illuminated by illumination beam 11 and area 14 is illuminated by illumination beam 12. As depicted in FIG. 2, there is an overlap between the areas illuminated by illumination beams 11 and 12 that are visible by the detector. Normally, this would result in undesirable interference. However, since the illumination of areas 13 and 14 are separated in time, interference is minimized.

Figure 3:
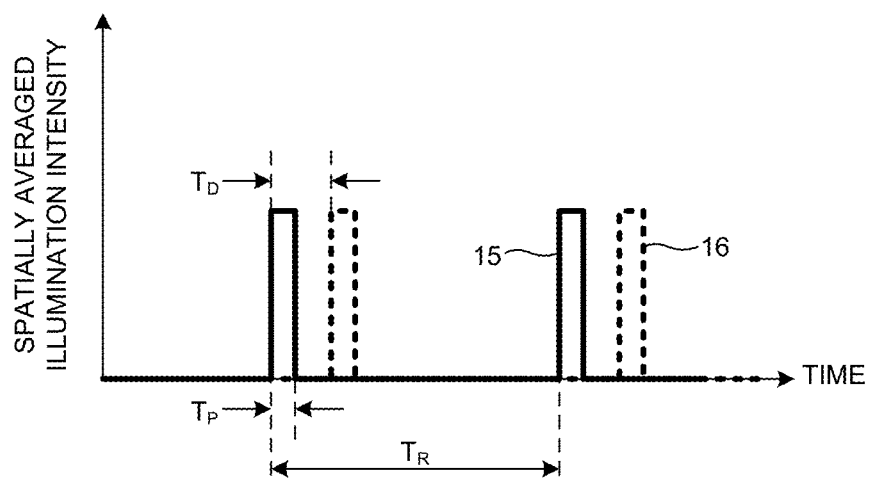
FIG. 3 is a representative plot illustrative of the illumination intensity averaged over different areas of a specimen illuminated by multiple beams.

FIG. 3 illustrates a representation of a time trace 15 of the illumination intensity averaged over area 13 and a time trace 16 of the illumination intensity averaged over area 14. As depicted in FIG. 3, each pulse of illumination light is characterized by a pulse width or pulse duration, $T_P$. In addition, the laser light source is also characterized by a repetition period, $T_R$. To minimize interference, the optical delay, $T_D$, introduced between the secondary illumination beams 11 and 12 must be larger than the pulse width of the illumination light 10. In addition, the optical delay must be smaller than the period between pulses. In some embodiments, the difference in path length among each secondary beam is approximately 10 millimeters. This results in approximately 30 picoseconds of optical delay. This is greater than the pulse duration of typical mode locked lasers useful for semiconductor inspection applications (e.g., 10-20 picoseconds), but well within the pulse repetition rate of these lasers (e.g., 50-200 MHz). In general, the conditions described herein should be met regardless of the number of secondary illumination beams and the particular performance specifications of the pulsed illumination source. In addition, the sensor integration time should be larger than the delay between the first and last pulses plus the pulse width. In practice sensor integration times longer than this minimum are often desirable in order to average over many pulses of the illumination source.

Figure 4:
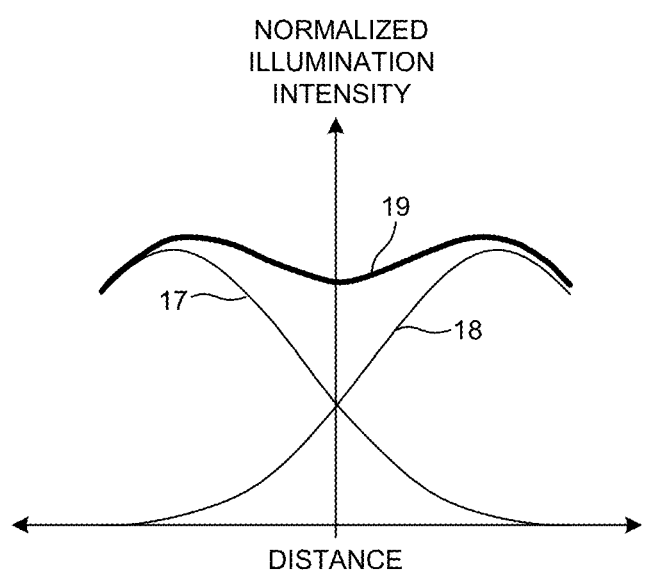
FIG. 4 is a representative plot illustrative of the illumination profiles of multiple illumination beams at the surface of a specimen and the overall, time-averaged illumination profile.

FIG. 4 depicts a representation of the illumination profile 17 across the long axis of illumination area 13 within the field of view 21 depicted in FIG. 2. Similarly, FIG. 4 also depicts a representation of the illumination profile 18 across the long axis of illumination area 14 within the field of view 21 depicted in FIG. 2. Finally, FIG. 4 also depicts the effective time-averaged illumination profile 19 across the long axis of the field of view 21 due to illumination by beams 11 and 12. In this manner an effective proxy of a flat top illumination beam is realized using two Gaussian beams with a minimum of wasted light and a minimum interference between the two beams.

The embodiment depicted in FIG. 1 is provided by way of non-limiting example. For example, input illumination light 10 may have any intensity distribution. In some examples, the distribution may be approximated as Gaussian. However, in some other examples, additional optical elements may be employed to further shape the intensity distribution of the beam of illumination light generated by the illumination source before splitting the illumination beam into multiple secondary beams. In another example, the optical subsystem 25 described with reference to FIG. 1 generates copies of the intensity distribution of the incoming beam 10. However, in general, an optical subsystem may include an arrangement of optical elements that generates multiple secondary beams that have been attenuated, subject to phase delay, or repositioned in space. In general, any optical subsystem that generates multiple illumination beams from an input illumination beam and introduces optical delay among the multiple illumination beams at the surface of the specimen under inspection may be contemplated within the scope of this patent document.

Figure 5:
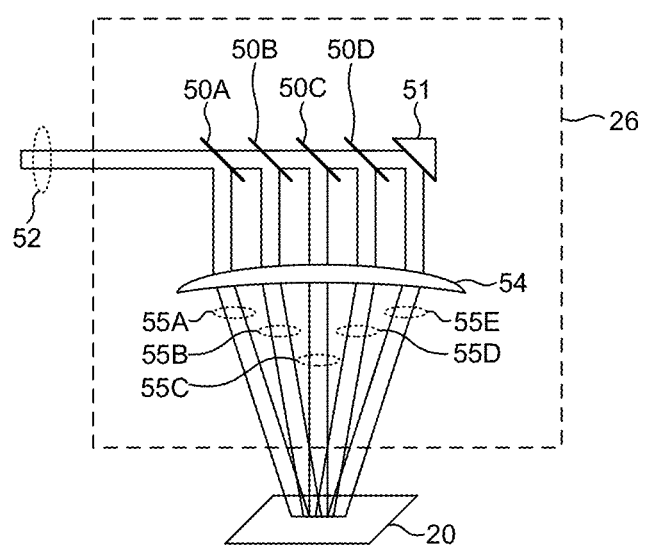
FIG. 5 is a simplified diagram illustrative of an optical subsystem configured to split a beam of incoming illumination light into secondary beams of illumination light that are temporally separated at the surface of the specimen under inspection in another embodiment.

FIG. 5 depicts an optical subsystem 26 configured to split a beam of incoming illumination light into secondary beams of illumination light that are temporally separated at the surface of the specimen under inspection in another embodiment. Optical subsystem 26 receives an amount of illumination light 52 generated by a pulsed illumination source (not shown). As depicted in FIG. 5, optical subsystem 26 includes a series of beam splitters 50A-50D and a mirror 51 that generate five secondary illumination beams 55A-55E. A refractive optical element 54 directs each of the illumination beams 55A-55E toward the surface of specimen 20 in the desired pattern. As depicted in FIG. 5, the path lengths of each of the illumination beams 55A-55E are different. For example, the distance between each beam splitter may be approximately 10 millimeters to generate approximately 30 picoseconds of optical delay between each illumination beam.

Figure 6:
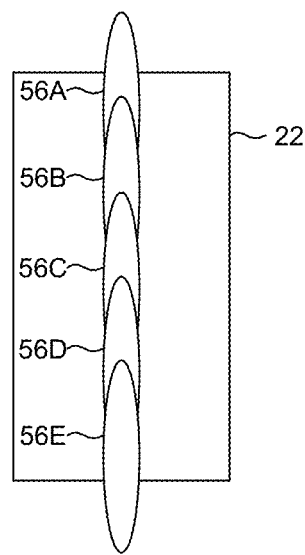
FIG. 6 is a simplified diagram illustrative of a portion of the surface of a specimen illuminated by the optical subsystem illustrated in FIG. 5.

FIG. 6 illustrates a portion 22 of the surface of specimen 20 within the field of view of a detector (not shown). Areas 56A-E are illuminated by illumination beams 55A-E, respectively. As depicted in FIG. 5, there is an overlap between the areas illuminated by each of the illumination beams 55A-E that are visible by the detector. Normally, this would result in undesirable interference. However, since the illumination of areas 56A-E are separated in time, interference is minimized.

Figure 7:
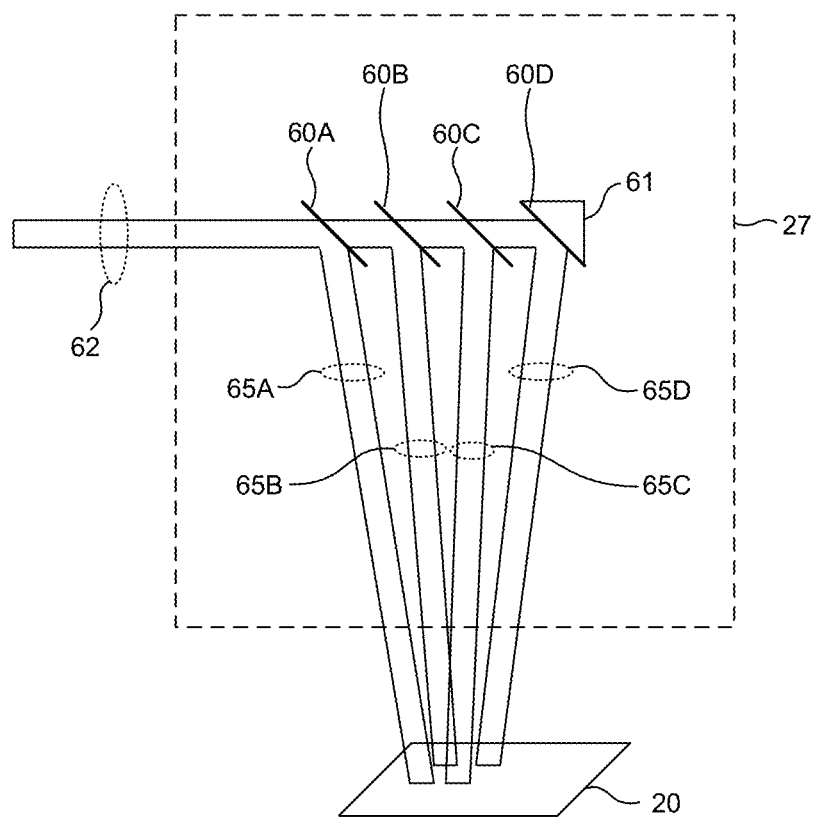
FIG. 7 is a simplified diagram illustrative of an optical subsystem configured to split a beam of incoming illumination light into secondary beams of illumination light that are temporally separated at the surface of the specimen under inspection in yet another embodiment.

FIG. 7 depicts an optical subsystem 27 configured to split a beam of incoming illumination light into secondary beams of illumination light that are temporally separated at the surface of the specimen under inspection in yet another embodiment. Optical subsystem 27 receives an amount of illumination light 62 generated by a pulsed illumination source (not shown). As depicted in FIG. 7, optical subsystem 27 includes a series of beam splitters 60A-60D of fixed orientation and appropriate split factors and a mirror 61 that generate four secondary illumination beams 65A-65D of approximately equal illumination power. In the depicted embodiment, beam splitters 60A-60D are individually aligned to direct each illumination beam directly to the desired locations on the surface of specimen 20. As depicted in FIG. 7, the path lengths of each of the illumination beams 65A-65D are different. For example, the distance between each beam splitter may be approximately 10 millimeters to generate approximately 30 picoseconds of optical delay between each illumination beam.

Figure 8:
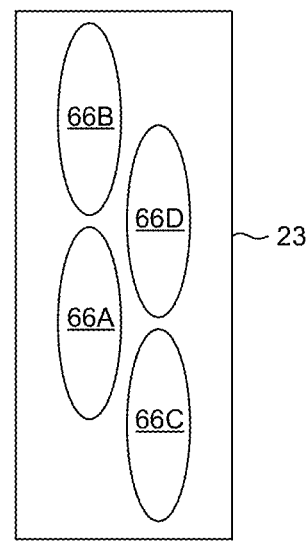
FIG. 8 is a simplified diagram illustrative of a portion of the surface of a specimen illuminated by the optical subsystem illustrated in FIG. 7.

FIG. 8 illustrates a portion 23 of the surface of specimen 20 within the field of view of a detector (not shown). Areas 66A-D are illuminated by illumination beams 65A-D, respectively. Since the illumination of each of areas 66A-D is separated in time, interference is minimized despite any spatial overlap.

In general, any number of illumination beams may be generated and arranged in any pattern on the surface of the specimen, either in accordance with the embodiments described herein, or by any other optical arrangement. As long as the optical subsystem is configured to illuminate each area separately in time, interference is minimized despite any spatial overlap among the areas of the surface of the specimen illuminated by each of the secondary illumination beams.

In another aspect, interferences among the multiple illumination beams are effectively mitigated by employing a time-delay integration (TDI) detector and an optical subsystem that generates multiple illumination beams from an illumination source having a non-uniform intensity distribution. The optical subsystem directs each of the multiple illumination beams to the surface of the specimen under inspection such that each area of the surface of the specimen illuminated by each beam is spatially separate from the others. The TDI detector receives an amount of light collected from each area of the specimen illuminated by each of the illumination beams. A point object imaged by the optical system onto the TDI detector moves across the detector surface with the same speed as the speed of transfer of charges through the detector. Since each illumination area is spatially separated, the point object of interest moves through any illumination areas in the path of the motion trajectory of the point object without interference. The image of the point object illuminated by each illumination area in its path moves across the TDI detector as the associated charge coupled device (CCD) charges are transferred across the detector. Thus, the point object of interest will interact with illumination light from each illumination spot in its motion trajectory and the interaction will be passed to the TDI detector, and integrated. In this manner, the relative position of the illumination spots along the direction of motion of the point object of interest has no impact on the illumination efficiency distribution over the field of view.

Figure 9:
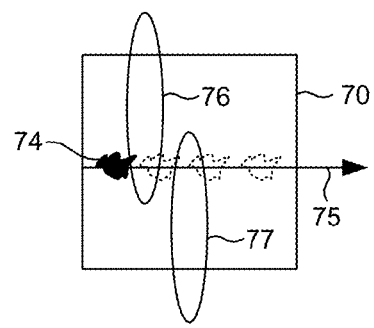
FIG. 9 is a simplified diagram illustrative of the trajectory of a point object of interest across the field of view of a time-delay integration (TDI) detector.

FIG. 9 illustrates the trajectory 75 of a point object of interest 74 across the field of view of a TDI detector 70. The point object of interest 74 is illuminated by two spatially separated illumination areas 76 and 77 imaged onto TDI detector 70. The pixels of TDI detector 70 are shifted in the horizontal direction across FIG. 9. In this manner, a uniform illumination is achieved in the vertical direction across FIG. 9. The total amount of light incident on, and hence the total amount of light reflected or scattered by, point object of interest 74 is substantially similar regardless of its vertical location within the field of view. Thus, the sensitivity of the inspection system is substantially independent of the vertical location of the point object of interest 74.

Spatial separation among illumination areas may be achieved by design of any of the optical subsystem embodiments described herein.

Figure 10:
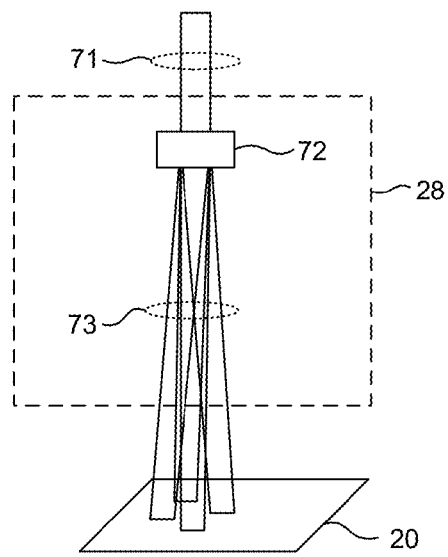
FIG. 10 is a simplified diagram illustrative of an optical subsystem configured to split a beam of incoming illumination light into secondary beams of illumination light that are spatially separated at the surface of the specimen under inspection in one embodiment.

FIG. 10 depicts an optical subsystem 28 configured to split a beam of incoming illumination light into secondary beams of illumination light that are spatially separated at the surface of the specimen under inspection in another embodiment. Optical subsystem 28 receives an amount of illumination light 71 generated by a pulsed illumination source (not shown). As depicted in FIG. 10, optical subsystem 28 includes a diffractive optical element 72 configured to generate four secondary illumination beams 73 of approximately equal illumination power and direct each illumination beam directly to the desired locations on the surface of specimen 20.

Figure 11:
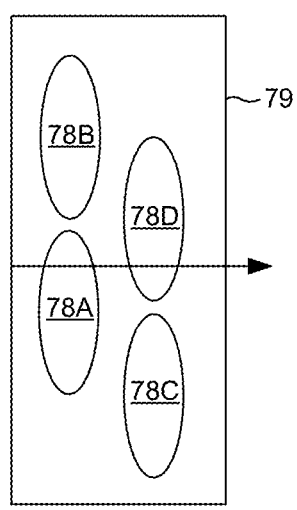
FIG. 11 is a simplified diagram illustrative of a portion of the surface of a specimen illuminated by the optical subsystem illustrated in FIG. 10.

FIG. 11 illustrates a portion 79 of the surface of specimen 20 within the field of view of a TDI detector. Areas 78A-D are illuminated by illumination beams 73. Since the illumination of each of areas 78A-D is spatially separated across the TDI detector, interference is minimized. Thus, the combined illumination profile is not sensitive to relative phase changes between beams and wave front errors. As described with respect to FIG. 9, the pixels of the TDI detector are shifted in the horizontal direction across FIG. 11. In this manner, a uniform illumination is achieved in the vertical direction across FIG. 11 as images of point objects of interest move across the sensor in the horizontal direction.

In general, any number of illumination spots may be contemplated within the scope of this patent document. In principle, imaging efficiency and non-uniformity are improved as the number of illumination spots increases. However, such improvements should be balanced by engineering considerations that may arise with a larger number of spots.

As described hereinbefore, interferences among the multiple illumination beams are effectively mitigated by employing a pulsed illumination source and an optical subsystem that introduces temporal delay among the multiple illumination beams at the surface of the specimen under inspection. This method is effective regardless of whether the areas illuminated by the beams are spatially separated of spatially overlapping.

In addition, as described hereinbefore, interferences among the multiple illumination beams are effectively mitigated by employing a time-delay integration (TDI) detector and an optical subsystem that generates multiple illumination beams and directs each of the multiple illumination beams to areas of the surface of the specimen that are spatially separate. This method is effective regardless of whether a pulsed or continuous illumination source is employed and regardless of whether temporal delay is introduced among multiple illumination beams at the surface of the specimen.

Thus, an inspection system employing any combination of the methods described hereinbefore effectively mitigates interferences among multiple illumination beams. For example, an inspection system employing a pulsed illumination source and an optical subsystem that introduces temporal delay among the multiple illumination beams at the surface of the specimen under inspection may also employ a TDI detector. In another example, an inspection system employing a time-delay integration (TDI) detector and an optical subsystem that directs multiple illumination beams to spatially separate areas of the surface of the specimen may also employ a pulsed laser source, an optical subsystem that introduces temporal delay among the multiple illumination beams at the surface of the specimen, or both.

In yet another aspect, an optical subsystem is employed to spatially split a pulsed Gaussian beam into at least two halves with a spatial displacement and time delay. Any two spatially overlapping half-Gaussian beams are delayed in time longer than the pulse length to avoid interference. The half-Gaussian beams are spatially displaced slightly so that the total intensity profile has a flat top around the center. In some examples, this results in a more effective use of illumination light. In some examples, the peak intensity of each pulse is reduced and the lifetime of optics and sensors is improved.

Figure 12:
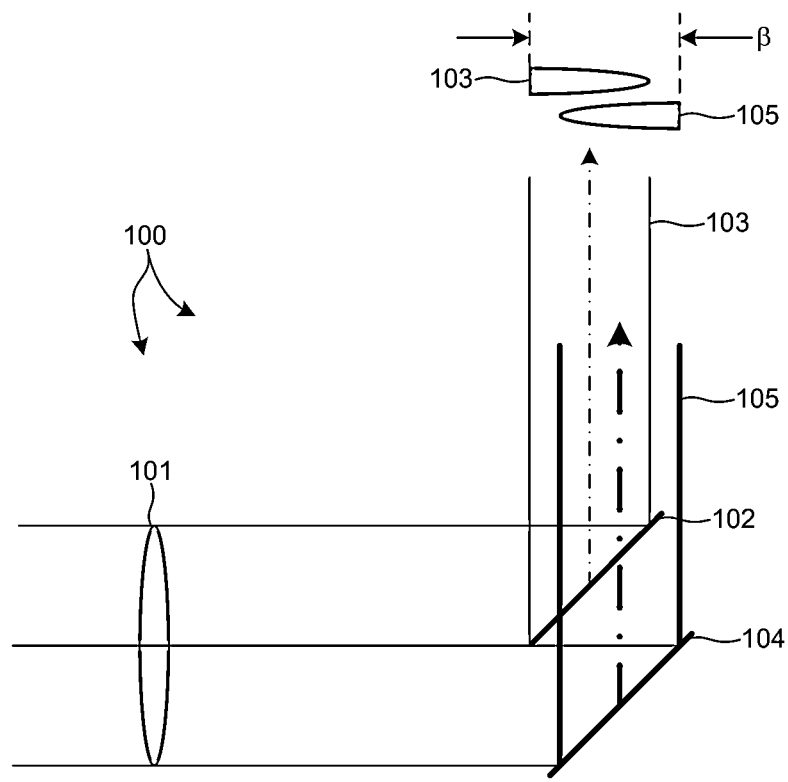
FIG. 12 is a simplified diagram illustrative of an optical subsystem configured to spatially split a beam of incoming illumination light into two halves with a spatial displacement and time delay in one embodiment.

FIG. 12 depicts an optical subsystem 100 configured to spatially split a beam of incoming illumination light into two halves with a spatial displacement and time delay in one embodiment. A pulsed illumination source generates a circular, or nearly circular, Gaussian beam of light. The beam of light is made elliptical by suitable optics (not shown). Optical subsystem 100 receives the elliptical beam of light 101. Optical subsystem 100 includes two parallel mirrors 102 and 104 arranged to split the beam 101 into two halves along the short axis. The elliptical Gaussian beam 101 is incident on parallel mirrors 102 and 104. The lower edge of mirror 102 approximately lines up with the optical rays at the center of the incoming Gaussian beam 101 so that only the upper half of the Gaussian beam is reflected by mirror 102. The reflected half Gaussian beam 103 is depicted in FIG. 12 with regular line weight. The lower half of the incoming Gaussian beam 101 travels slightly further and is reflected by mirror 104 at the same incidence angle. The reflected half Gaussian beam 105 is depicted in FIG. 12 with heavy line weight. Mirrors 102 and 104 are tilted out of the plane of FIG. 12 to prevent mirror 102 from blocking beam 105 and to slightly displace the two beams in a direction parallel to their short axes. The spatial displacement of the two beams should be chosen so that both are imaged onto the sensor. Reflected beams 103 and 105 are depicted in a shaded view in FIG. 12 as viewed from the direction of propagation, i.e. the beam profile on the wafer plane and as re-imaged onto the sensor plane. In some embodiments, rays near the lower edge of mirror 102 may be apodized or filtered out to reduce diffraction and/or scattering.

The two half-Gaussian beams 103 and 105 are both spatially displaced and temporally delayed with respect to one another. The temporal delay is greater than the pulse duration to avoid interference. In a preferred embodiment the relative displacement, $\beta$, of the two beams in a direction parallel to their long axes should be between approximately $1w_0$ and $1.1w_0$, where $w_0$ is the Gaussian beam waist. In this manner, the minimum intensity in the overlap region is about 95%, or more, of the peak intensity. For such an overlap, approximately 95% of the energy of the laser beam is in the overlap region.

In some embodiments, TDI sensors scan the signal along the short axes of the beams 103 and 105 and integrate the signal over a finite time period. The integration time should be at least five times longer than the time between successive laser pulses. In this manner, the intensity profile measured by TDI sensors is essentially the sum of the two half-Gaussian beam profiles. The combination of the two beams generates a substantially uniform optical field. Most of the energy is distributed substantially uniformly around the top and thus can be used directly for inspection purposes.

Figure 13:
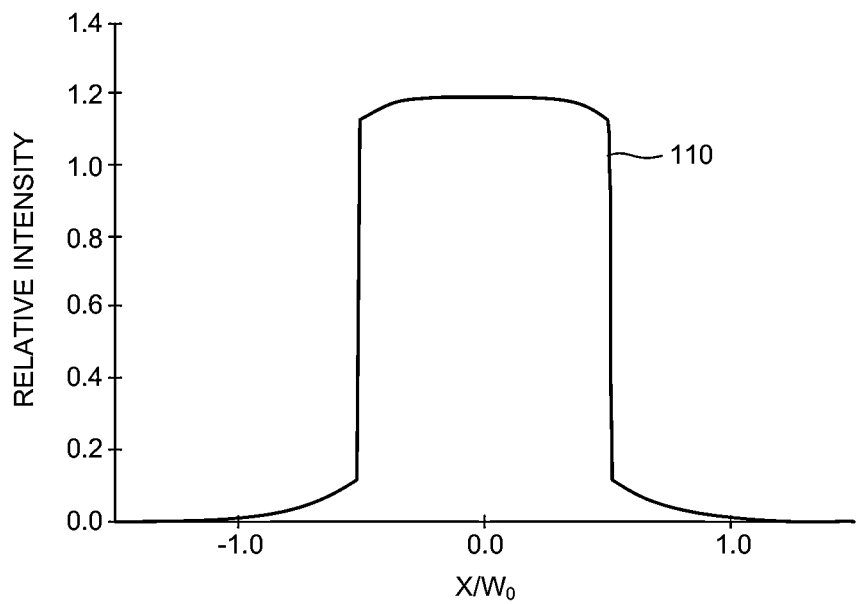
FIG. 13 is a representative plot illustrative of the overall, time-averaged illumination profile generated by the optical subsystem illustrated in FIG. 12.

The illumination intensity as collected by a TDI sensor integrating over time has a substantially flat-top profile. FIG. 13 illustrates an intensity profile 110 for a relative displacement, $\beta$, of $1.02w_0$, where $w_0$ is the Gaussian beam waist. The full width of the substantially flat portion of the signal is β. Thus, most of the energy of the beams (approximately 95%) is within the substantially flat portion of the illumination intensity profile.

In some embodiments, the angle of incidence on the mirrors is 45 degrees. However, in general, any angle of incidence may be chosen to optimize beam separation in time and space given the constraints of the sensor size, integration time, and optics layout.

Figure 14:
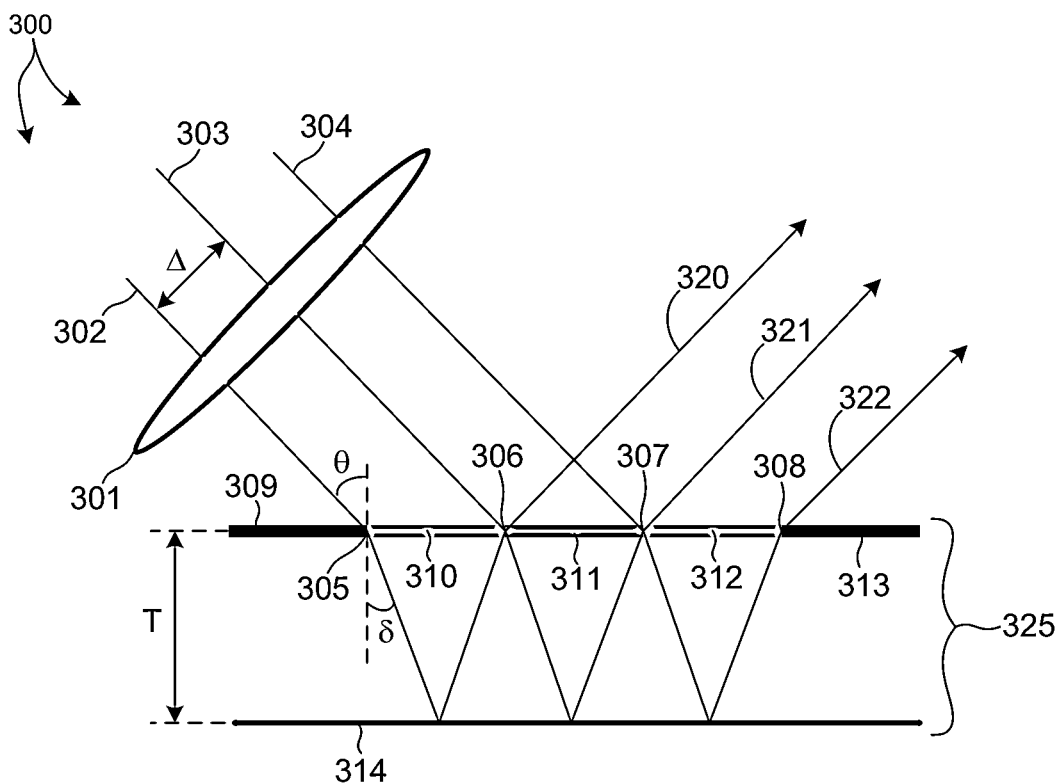
FIG. 14 is a simplified diagram illustrative of an optical subsystem configured to spatially split a beam of incoming illumination light into multiple half-beams in one embodiment.

FIG. 14 depicts an optical subsystem 300, in one embodiment, configured to spatially split a beam of incoming illumination light into four halves, each with approximately equal intensity, and each with a time delay with respect to the others. In addition, two of the four halves are spatially separated from the other two halves.

A pulsed illumination source generates a circular, or nearly circular, Gaussian beam of light. The beam of light is made elliptical by suitable optics (not shown). Optical subsystem 300 receives the elliptical beam of light 301. Optical subsystem 300 includes a parallel beam plate structure 325. The incoming beam of light 301 is incident on parallel beam plate 325 and eventually fully reflected from the parallel beam plate structure 325. The average intensity profile of the reflected beam has a substantially flat top with reduced peak intensity.

Parallel beam plate 325 has different coating properties in different areas on the front surface and a high reflective coating on the back surface. Ideally, no light is transmitted through the back surface of parallel beam plate 325. In some embodiments, parallel beam plate 325 is constructed from fused silica.

Rays at several different positions are labeled in FIG. 14 for reference. Ray 303 is at the center of the incoming Gaussian beam 301. Ray 302 is a distance, Δ, away from the center on the left, and ray 304 is a distance, Δ, away from the center on the right along the long axis of the ellipse. Rays 302, 303 and 304 are incident on the front surface of the plate at points 305, 306, and 307, respectively. Area 310, between points 305 and 306 on the front surface, is coated for high transmission. Rays between rays 302 and 303 are transmitted into the beam plate and are reflected from back surface 314. Area 311, between points 306 and 307, is coated for approximately 50% transmission and approximately 50% reflection. Rays between rays 303 and 304 are 50% reflected directly from the front surface and 50% transmitted through the front surface. The rays that are transmitted through the front surface travel to the back surface 314 where they are reflected back towards the front surface. Point 308 corresponds to the point where the ray 304 hits the front surface after reflection from the back surface 314. Area 312 on the front surface, between points 307 and 308, is also coated for high transmission, similar to area 310. Area 309 to the left of point 305 and area 313 to the right of point 308 are coated as apodizers. The thickness, T, of the plate is chosen so that ray 302, after reflection from the back surface, transmits through the front surface at substantially point 306, where ray 303 is reflected from the front surface. These rays are labeled 320. The transmission of ray 303 through the front surface, after reflection from the back surface, is also substantially aligned with the reflection of ray 304 from the front surface (at point 307) and is labeled 321. Ray 304, after reflection from the back surface and subsequent transmission through the front surface is labeled 322.

Effectively the Gaussian beam is spatially split into two halves at its center. One half is spatially shifted and time-delayed with respect to the other half. Each half-Gaussian beam is intensity-split from the 50/50 beam splitting coating and shifted the same distance, Δ.

To spatially shift one half-Gaussian beam with respect to the other half-Gaussian by the distance, Δ, and overlap, the thickness, T, the refractive index n, the incident angle, θ, and the beam waist of the incident Gaussian beam, $w_0$, must satisfy equation (1).

$$t = \Delta*(n^2 - \sin^2 \theta)^{1/2}/(2*\sin \theta * \cos \theta) \quad (1)$$

If the incident angle 45 degrees, equation (1) simplifies to $t = \Delta*(n^2 - 0.5)^{1/2}$. In some embodiments, the beam waist, $w_0$, and the incident angle, θ, may be adjusted slightly to optimize the reflected beam profile after the parallel beam plate is designed.

Figure 15:
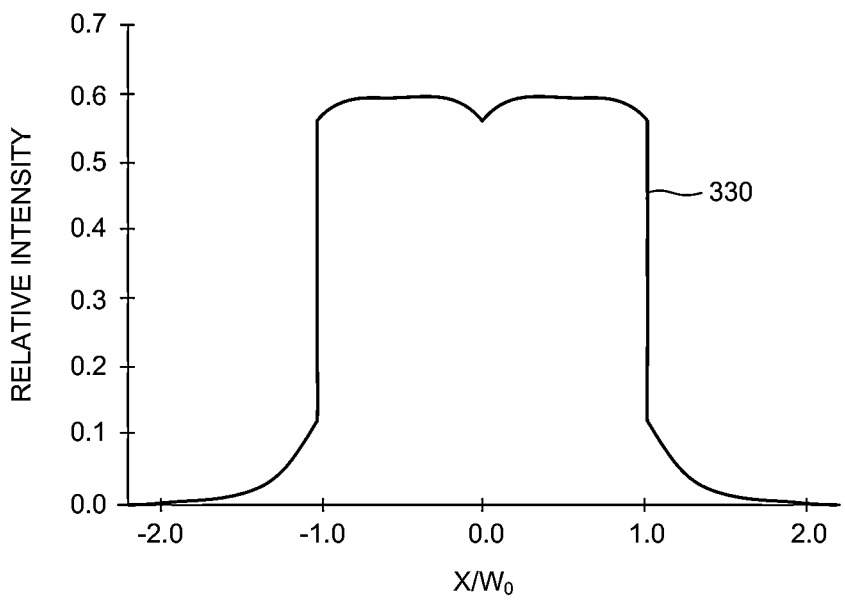
FIG. 15 is a representative plot illustrative of the overall, time-averaged illumination profile generated by the optical subsystem illustrated in FIG. 14.

FIG. 15 illustrates the intensity profile of the reflected beam from the parallel beam plate for the case of $\Delta = 1.02 w_0$. It is substantially similar to that shown in FIG. 13 but with two of the flat regions depicted in FIG. 13 placed side by side. In this example, the full width of the substantially flat portion of the light reflected from parallel beam plate 325 is 2Δ; twice the width illustrated in FIG. 13. In addition, the intensity at the flat top is about half of that generated by the embodiment of FIG. 12 for the same value, Δ.

In a preferred embodiment, Δ, should be between approximately $1w_0$ and $1.1w_0$, where $w_0$ is the Gaussian beam waist, so that the minimum intensity in the overlap region is about 95%, or more, of the peak intensity. For such an overlap, approximately 95% of the energy of the laser beam is in the overlap region. If the system could tolerate a greater than 5% intensity variation within the overlap region, the range of the displacement, Δ, may be extended.

FIG. 15 illustrates one exemplary shape of the tails of the distribution. The shape of the tails depends on the design of the apodizers. In some embodiments, the tails could be totally filtered out if needed.

The time delay between the two half Gaussians is $2*n^2*t*(n^2 - \sin^2 \theta)^{-1/2} c^{-1}$, where c is the velocity of light in vacuum. For example, if the angle of incidence is 45° and the refractive index of the beam plate material is 1.5 (such as fused silica at a wavelength near 266 nm), then a beam plate thickness, T, of 5 mm would result in a time delay of 57 ps. If the pulse length is less than 57 ps, then this delay would be sufficient to avoid interference of one half Gaussian with another. Such a beam plate would shift one half Gaussian with respect to another by 3.8 mm, and would be appropriate if the long axis of the elliptical Gaussian beam waist at the beam plate is approximately 3.6 mm.

In another embodiment, a parallel beam plate is configured split an incoming illumination beam into four half-beams. In addition, the parallel beam plate is configured to emit two of the four half-beams from a front surface of the parallel beam plate and the remaining two half-beams from a back surface, opposite the front surface. In this manner, the parallel beam plate is configured to generate two channels of illumination light, each having an effectively uniform intensity distribution. In some embodiments, the two channels may be employed to illuminate the surface of a specimen under inspection in two different locations, two different angles of incidence, etc. at the same time.

Figure 16:
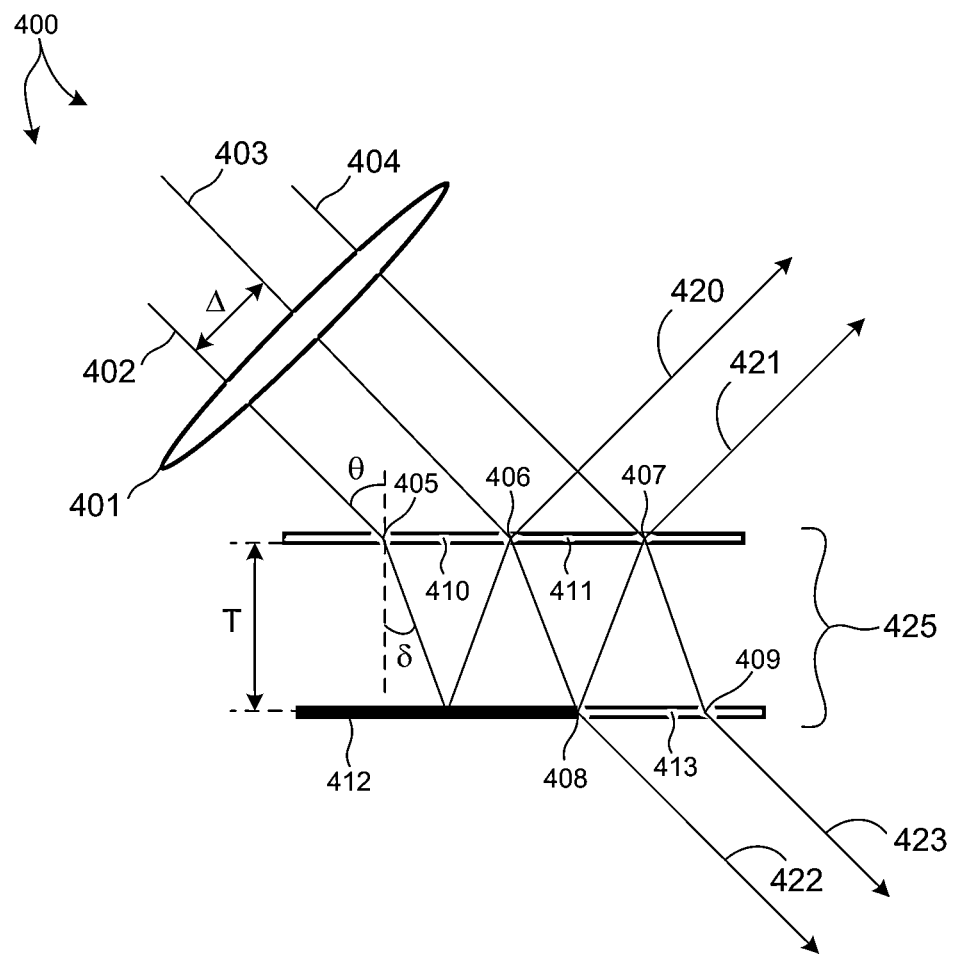
FIG. 16 is a simplified diagram illustrative of an optical subsystem configured to spatially split a beam of incoming illumination light into multiple half-beams in another embodiment.

FIG. 16 depicts an optical subsystem 400 configured to spatially split a beam of incoming illumination light into four halves with a spatial displacement and time delay over two output channels in one embodiment.

A pulsed illumination source generates a circular, or nearly circular, Gaussian beam of light. The beam of light is made elliptical by suitable optics (not shown). Optical subsystem 400 receives the elliptical beam of light 401. Optical subsystem 400 includes a parallel beam plate structure 425. The incoming beam of light 401 is incident on parallel beam plate 425 and is eventually both reflected from and transmitted through parallel beam plate structure 425. The average intensity profiles of the reflected beam and the transmitted beam have a substantially flat top with reduced peak intensity. Parallel beam plate 425 has different coating properties in different areas on the front surface and the back surface. In some embodiments, parallel beam plate 425 is constructed from fused silica.

Rays at several different positions are labeled for reference in FIG. 16. Ray 403 is at the center of the incoming Gaussian beam 401. Ray 402 is a distance, $\Delta$, away from the center on the left and ray 404 is distance, $\Delta$, away from the center on the right along the long axis of the elliptically shaped beam 401. Rays 402, 403, and 404 are incident on the front surface of the plate at points 405, 406, and 407, respectively. Area 410 includes the portion of the front surface located on the left side of point 406 as depicted in FIG. 16. Area 410 is coated for high transmission. Area 411 includes the portion of the front surface located on the right side of point 406 as depicted in FIG. 16. Area 411 is coated for 50% transmission and 50% reflection. Point 408 is where ray 403 is incident on the back surface. Area 412 includes the portion of the back surface to the left side of point 408 as depicted in FIG. 16. Area 412 is coated for high reflection. Area 413 includes the portion of the back surface to the right side of point 408 as depicted in FIG. 16. Area 413 is coated for high transmission. As a result, the left half-Gaussian beam is reflected from the back surface after transmission through the front surface and then 50% of the intensity transmits through the area 411 on the front surface and the other 50% is reflected from the front surface and transmits through area 413 of the back surface. The right half-Gaussian beam is 50% reflected from the front surface over area 411 and 50% transmits through both area 411 and area 413. The thickness of parallel plate 425 is chosen so that ray 402, after reflection from the back surface, transmits through the front surface at substantially point 406. At this same point, ray 403 is reflected from the front surface. These rays are labeled as 420. In addition the transmission of ray 403 through the front surface, after reflection from the back surface, is also substantially aligned with the reflection of ray 404 from the front surface at point 407. These rays are labeled 421. In the meantime, the transmission of ray 402 through the back surface, after reflection from the back surface over area 412 and reflection from the front surface over area 411, is substantially aligned with the transmission of ray 403 through both surfaces (at point 408). This ray is labeled 422. Similarly, the transmission of ray 403 though the back surface, after reflection from the back and front surfaces, is substantially aligned with the transmission of ray 404 through both surfaces at point 409. This ray is labeled 423. Effectively, the Gaussian beam is spatially split into two halves at the center over two output channels. One half-Gaussian beam is spatially shifted and time-delayed with respect to the other half-Gaussian beam. In addition, the overall beam is split in intensity between the two channels. 50% of the intensity is reflected from the parallel beam plate 425 and the other 50% transmits through the parallel beam plate 425. As a result, both outputs have a flat top substantially similar as shown in FIG. 13 with a width of $\Delta$, and each output contains approximately half the power of the input beam.

To spatially shift one half-Gaussian beam with respect to the other half-Gaussian by the distance, $\Delta$, and overlap, the thickness, T, the refractive index n, the incident angle, $\theta$, and the beam waist of the incident Gaussian beam, $w_0$, must satisfy equation (1).

In some embodiments, the beam waist, $w_0$, and the incident angle, $\theta$, may be adjusted slightly to optimize the reflected beam profile after the parallel beam plate is designed.

In a preferred embodiment, $\Delta$, should be between approximately $1w_0$ and $1.1w_0$, where $w_0$ is the Gaussian beam waist, so that the minimum intensity in the overlap region is about 95%, or more, of the peak intensity. For such an overlap, approximately 95% of the energy of the laser beam is in the overlap region. If the system could tolerate a greater than 5% intensity variation within the overlap region, the range of the displacement, $\Delta$, may be extended.

The time delay between the two half Gaussians is $2*n^2*t*(n^2-\sin^2\theta)^{-1/2}c^{-1}$, where c is the velocity of light in vacuum. For example, if the angle of incidence is 45° and the refractive index of the beam plate material is 1.5 (such as fused silica at a wavelength near 266 nm), then a beam plate thickness, T, of 5 mm would result in a time delay of 57 ps. If the pulse length is less than 57 ps, then this delay would be sufficient to avoid interference of one half Gaussian with another. Such a beam plate would shift one half Gaussian with respect to another by 3.8 mm, and would be appropriate if the long axis of the elliptical Gaussian beam waist at the beam plate is approximately 3.6 mm.

In a preferred embodiment, the coating around the splitting edges is tapered or profiled so that diffraction and/or scattering are reduced.

Figure 17:
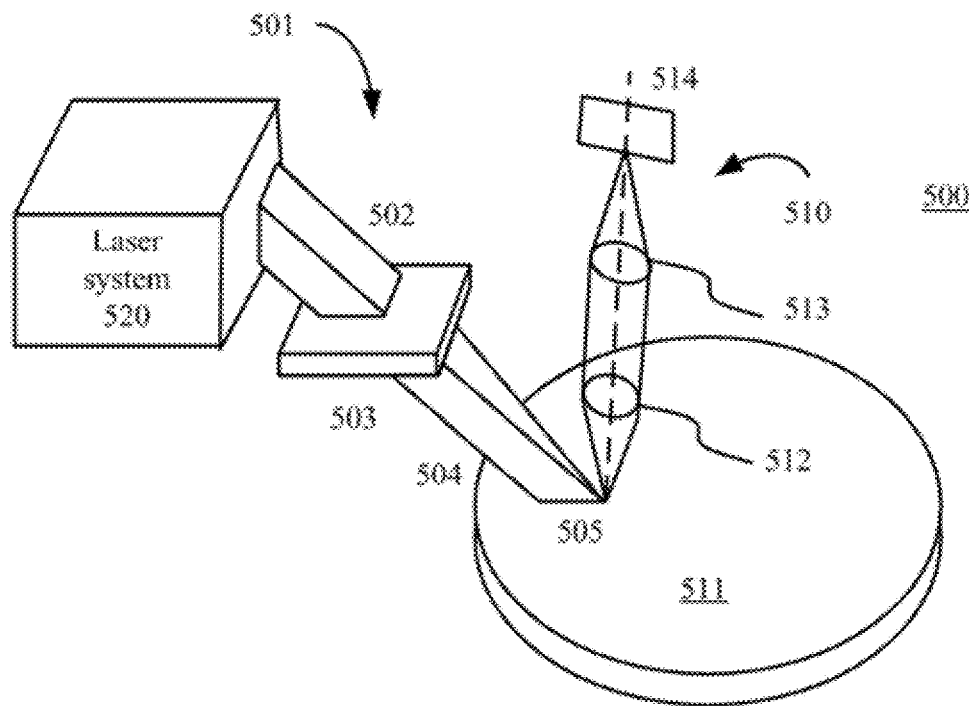
FIG. 17 is a simplified diagram illustrative of an inspection system 500 that may be configured in accordance with the methods and systems presented herein.
Figure 18:
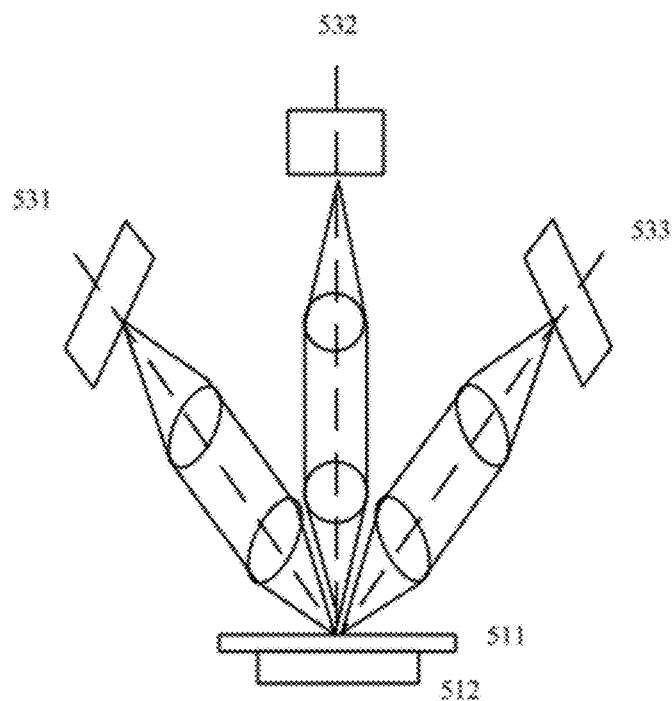
FIG. 18 is a simplified diagram illustrative of an embodiment of inspection system 500 having multiple collection paths.

The inspection and beam shaping techniques described herein may be employed in a dark-field inspection system with oblique line illumination as depicted in FIG. 17. The inspection system may multiple collection systems including off axis and near normal collection as depicted in FIG. 18.

FIG. 17 is a simplified schematic view of one embodiment of an inspection system 500 that may be configured as described herein. For simplification, some optical components of the system have been omitted. By way of example, folding mirrors, polarizers, beam forming optics, additional light sources, additional collectors, and additional detectors may also be included. All such variations are within the scope of the invention described herein. The inspection system described herein may be used for inspecting patterned, as well as unpatterned wafers.

Inspection system 500 includes an illumination system 501 and a collection system 510 for inspecting areas of surface 511. As shown in FIG. 17, a laser system 520 directs a light beam 502 through beam shaping optics 503. In a preferred embodiment, the illumination system 501 includes an optical subsystem configured to minimize interference among multiple illumination beams as described herein. In some embodiments, beam shaping optics 503 are configured to receive a beam from the laser system, focus it to an elliptical profile, and apply the techniques described herein to generate a beam with an effectively uniform intensity profile that is focused onto surface 511.

Beam shaping optics 503 is oriented so that its principal plane is substantially parallel to a sample surface 511 and, as a result, illumination line 505 is formed on surface 511 in the focal plane of beam shaping optics 503. In addition, light beam 502 and focused beam 504 are directed at a non-orthogonal angle of incidence to surface 511. In particular, light beam 502 and focused beam 504 may be directed at an angle between about 1 degree and about 85 degrees from a normal direction to surface 511. In this manner, illumination line 505 is substantially in the plane of incidence of focused beam 504. The intensity profile along the long axis of line 505 is substantially flat through the use of the above described techniques.

Collection system 510 includes lens 512 for collecting light scattered from illumination line 505 and lens 513 for focusing the light coming out of lens 512 onto a device, such as charge coupled device (CCD) 514, comprising an array of light sensitive detectors. In one embodiment, CCD 514 may include a linear array of detectors. In such cases, the linear array of detectors within CCD 514 can be oriented parallel to illumination line 505. In one embodiment, multiple collection systems can be included, wherein each of the collection systems includes similar components, but differ in orientation.

Although the collection system 510 depicted in FIG. 17 illustrates a single collection channel, in general, any number of collection channels may be contemplated. For example, FIG. 18 illustrates an exemplary array of collection systems 531, 532, and 533 for a surface inspection apparatus (wherein its illumination system, e.g. similar to that of illumination system 501, is not shown for simplicity). First optics in collection system 531 collect light scattered in a first direction from the surface of sample 511. Second optics in collection system 532 collect light scattered in a second direction from the surface of sample 511. Third optics in collection system 533 collect light scattered in a third direction from the surface of sample 511. Note that the first, second, and third paths are at different angles of reflection to said surface of sample 511. A platform 512 supporting sample 511 can be used to cause relative motion between the optics and sample 511 so that the whole surface of sample 511 can be scanned. U.S. Pat. No. 7,525,649, which issued on Apr. 28, 2009, and is incorporated by reference herein, describes surface inspection apparatus 500 and other multiple collection systems in further detail.

Figure 19:
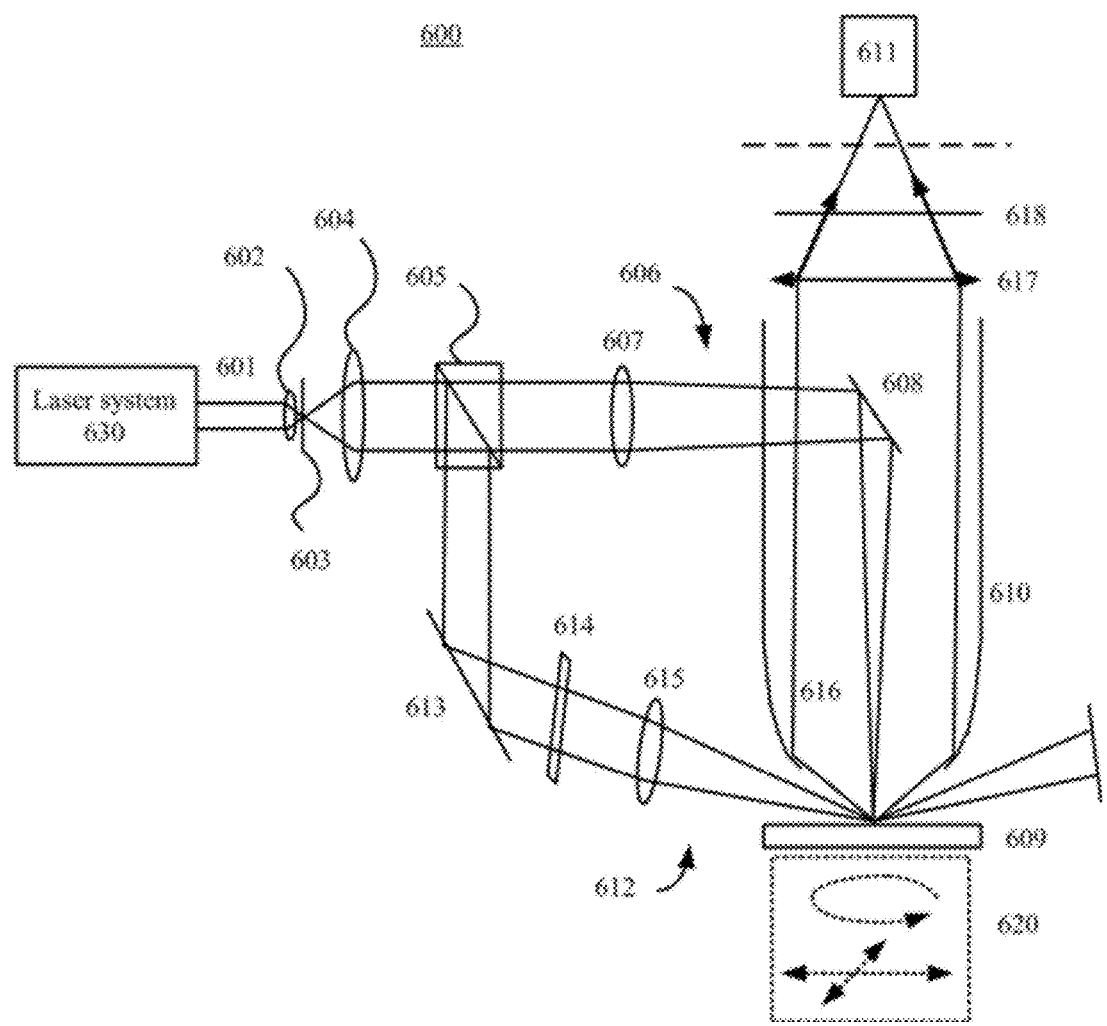
FIG. 19 is a simplified diagram illustrative of an inspection system 600 that may be configured in accordance with the methods and systems presented herein.

The inspection and beam shaping techniques described herein may be employed in inspection systems for unpatterned wafers such as system 600 depicted in FIG. 19. Such an inspection system may incorporate oblique and/or normal incidence illumination and a large collection solid angle for the scattered light.

Inspection system 600 is configured to implement anomaly detection using both normal and oblique illumination beams. In this configuration, a laser system 630 provides a laser beam 601. A lens 602 focuses the beam 601 through a spatial filter 603, and lens 604 collimates the beam and conveys it to a beam splitter 605. In a preferred embodiment, the illumination system 600 includes any of the inspection and beam shaping techniques described herein. For example, beam splitter 605 could be the beam plate of FIG. 16 and lens 602 and 604 could include cylindrical lenses configured to make the beam an elliptical profile, so that both beams after 605 have flat illumination profiles that contain a much higher percentage of laser light compared with truncation of the broad Gaussian profile with spatial filter 603.

Splitter 605 passes a first component to the normal illumination channel and a second component to the oblique illumination channel. In the normal illumination channel 606, the first component is focused by optics 607 and reflected by mirror 608 towards a surface of a sample 609. The radiation scattered by sample 609 is collected and focused by a paraboloidal mirror 610 to a line sensor 611 oriented parallel to the illumination line, in a similar manner to that shown in FIG. 17.

In the oblique illumination channel 612, the second component is reflected by beam splitter 605 to a mirror 613 which reflects such beam through a half-wave plate 614 and focused by optics 615 to sample 609. Radiation originating from the oblique illumination beam in the oblique channel 612 and scattered by sample 609 is also collected by paraboloidal mirror 610 and focused to line sensor 611. Note that line sensor 611 may have a slit entrance. The slit and the illuminated line (from the normal and oblique illumination channels on surface 609) are preferably at the foci of the paraboloidal mirror 610.

The paraboloidal mirror 610 collimates the scattered radiation from sample 609 into a collimated beam 616. Collimated beam 616 is then focused by an objective 617 and through an analyzer 618 to the line sensor 611. Note that curved mirrored surfaces having shapes other than paraboloidal shapes may also be used. An instrument 620 can provide relative motion between the beams and sample 609 so that spots are scanned across the surface of sample 609. U.S. Pat. No. 6,201,601, which issued on Mar. 13, 2001, and is incorporated by reference herein, describes inspection system 600 in further detail.

In general, the methods and optical subsystems described herein benefit not only imaging system, but also non-imaging systems. Such non-imaging systems typically rely on small spot illumination. In these systems, multi-spot illumination achieved in accordance with the methods and subsystems described herein provides an effective increase in pulse length, or effectively laser pulse repetition rate, as well as a reduced peak power over the illumination spot. As a result, in thermal-damage limited applications, the limits on light dosage could be raised. At the same time, uniformity of power delivery over the surface could be improved. In some embodiments, beam-splitting mirrors can be selectively moved into the beam only as necessary.

In some embodiments, an inspection system employing any combination of the methods described herein to effectively mitigate interferences among multiple illumination beams may employ a Q-switched laser or a mode-locked laser operating in the UV or deep UV range. The output from such a laser system is typically a Gaussian beam with good beam quality. In some embodiments, the laser may be generated from the high harmonics of a fundamental infrared laser that is configured to generate a fundamental frequency. For example if the fundamental laser generates a wavelength of 1064 nm, the fourth harmonic frequency will correspond to a wavelength of 266 nm and the fifth harmonic frequency will correspond to a wavelength of approximately 213 nm.

In yet another aspect, the illumination light may be scanned rapidly over a TDI detector to effectively flatten the intensity distribution of the illumination light as imaged onto the TDI detector. In some embodiments, an electro-optical crystal or mirror, mounted on a piezo-element may be used to scan the beam over the TDI detector. An effectively uniform distribution over the detector may be achieved if the scan time is less than the TDI integration time.

Figure 20:
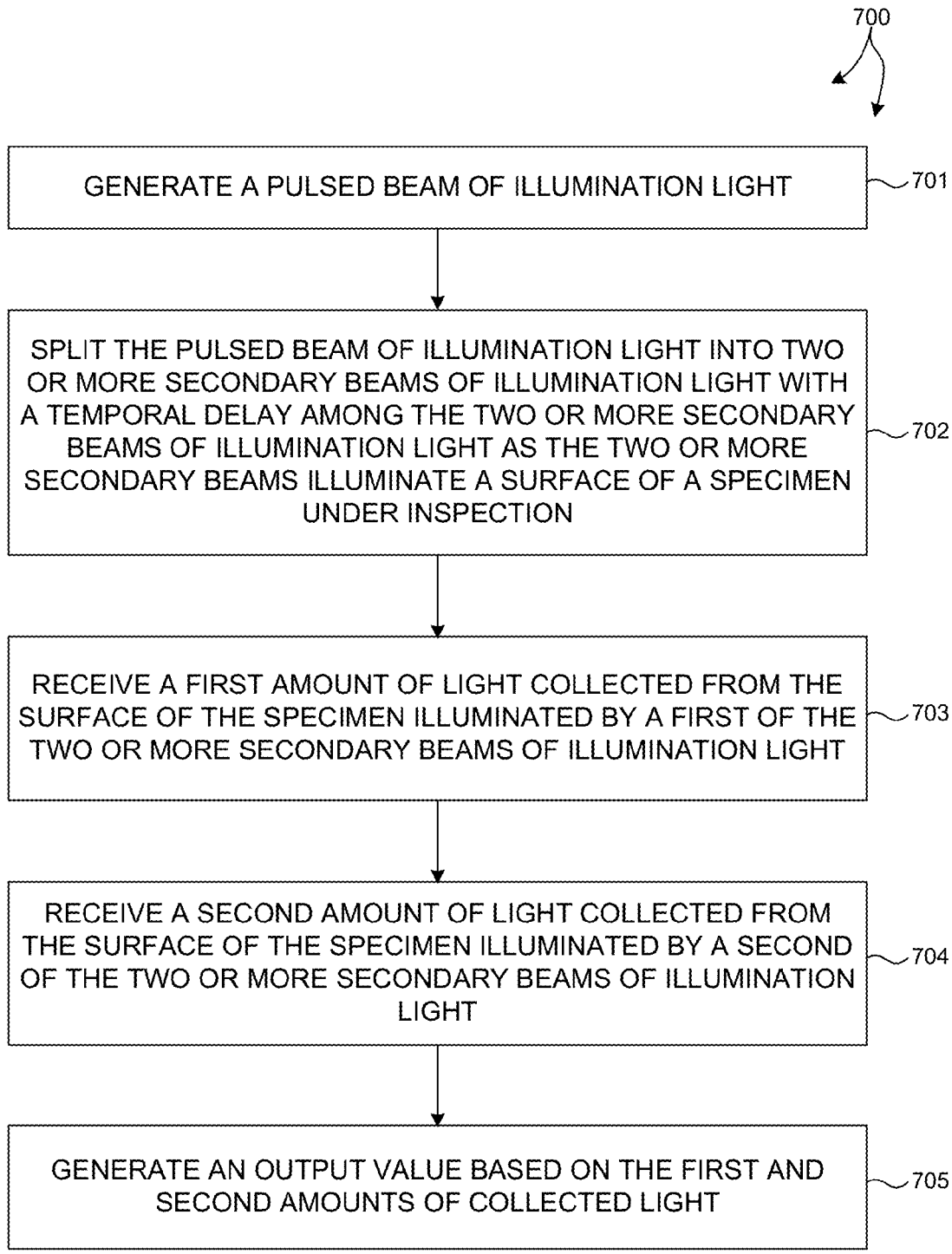
FIG. 20 is a flowchart illustrative of a method 700 of minimizing interference among multiple illumination beams.

FIG. 20 illustrates a flowchart of an exemplary method 700 useful for minimizing interference among multiple illumination beams. In one non-limiting example, inspection system 500, described with reference to FIG. 17 is configured to implement method 700. However, in general, the implementation of method 700 may be implemented by any of the subsystems and systems described, and furthermore is not limited by the specific embodiments described herein.

In block 701, a pulsed beam of illumination light is generated by a pulsed illumination source.

In block 702, the pulsed beam of illumination light is split into two or more secondary beams of illumination light such that a temporal delay exists among the two or more secondary beams of illumination light as the two or more secondary beams illuminate a surface of a specimen under inspection.

In block 703, a first amount of light collected from the surface of the specimen illuminated by a first of the two or more secondary beams of illumination light is received, for example, by a detector.

In block 704, a second amount of light collected from the surface of the specimen illuminated by a second of the two or more secondary beams of illumination light is received, for example, by the detector.

In block 705, an output value is generated based on the first and second amounts of collected light.

Figure 21:
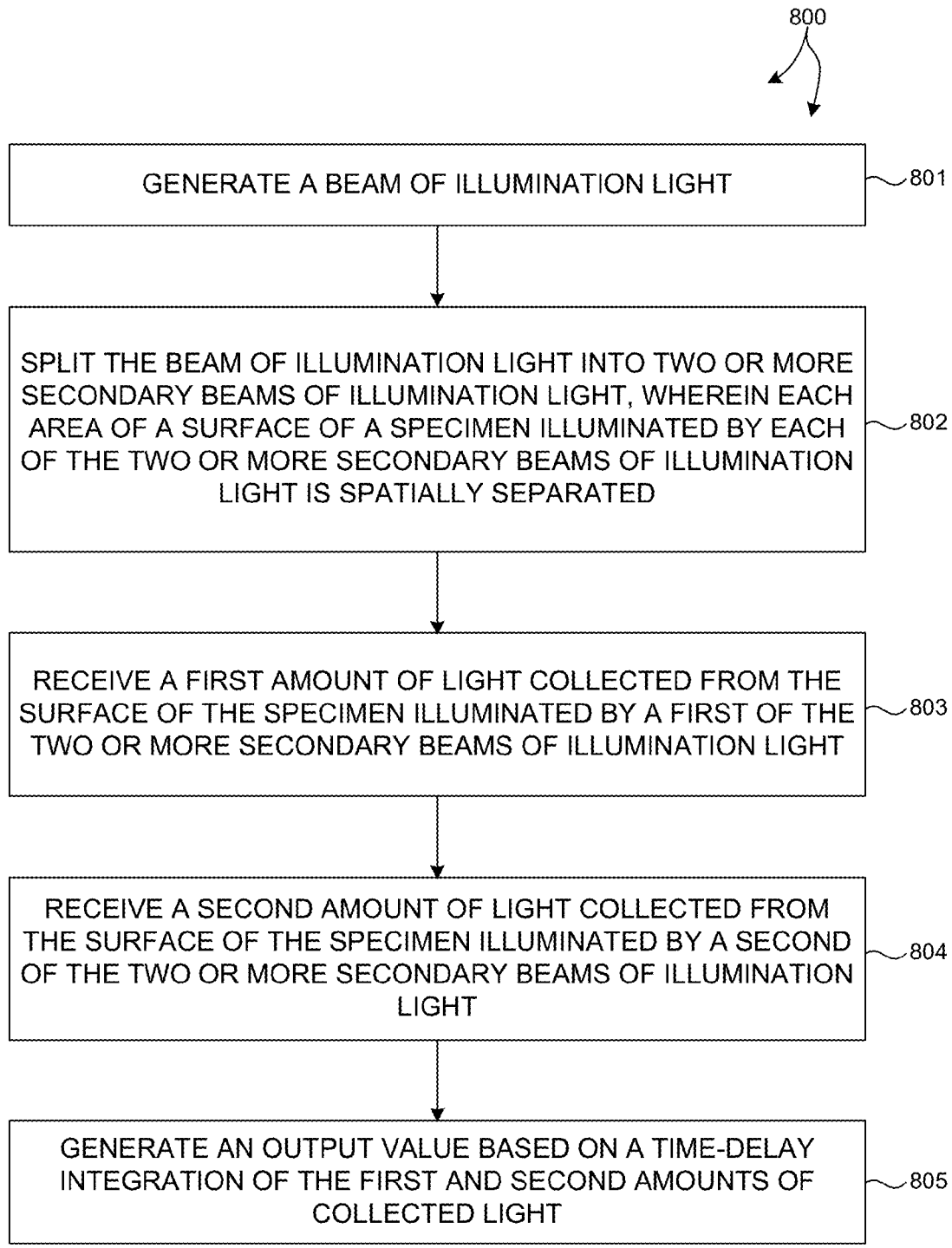
FIG. 21 is a flowchart illustrative of a method 800 of minimizing interference among multiple illumination beams.

FIG. 21 illustrates a flowchart of another exemplary method 800 useful for minimizing interference among multiple illumination beams. In one non-limiting example, inspection system 500, described with reference to FIG. 17 is configured to implement method 800. However, in general, the implementation of method 800 may be implemented by any of the subsystems and systems described, and furthermore is not limited by the specific embodiments described herein.

In block 801, a beam of illumination light is generated by an illumination source.

In block 802, the beam of illumination light is split into two or more secondary beams of illumination light, wherein each area of a surface of a specimen illuminated by each of the two or more secondary beams of illumination light is spatially separated.

In block 803, a first amount of light collected from the surface of the specimen illuminated by a first of the two or more secondary beams of illumination light is received, for example, by a detector.

In block 804, a second amount of light collected from the surface of the specimen illuminated by a second of the two or more secondary beams of illumination light is received, for example, by the detector.

In block 805, an output value is generated based on a time-delay integration of the first and second amounts of collected light.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the tem "wafer" generally refers to substrates formed of a semiconductor or non-semiconductor material. Examples include, but are not limited to, monocrystalline silicon, gallium arsenide, gallium nitride and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An inspection system comprising:
a pulsed laser illumination source configured to generate a beam of illumination light;
an optical subsystem that receives the beam of illumination light and splits the beam of illumination light into two or more secondary beams of illumination light, wherein the optical subsystem introduces a temporal delay among the two or more secondary beams of illumination light as the two or more secondary beams illuminate a surface of a specimen under inspection; and
a detector operable to receive a first amount of light collected from the surface of the specimen illuminated by a first of the two or more secondary beams of illumination light, receive a second amount of light collected from the surface of the specimen illuminated by a second of the two or more secondary beams of illumination light, and generate an output value based on an integration of the first and second amounts of light for a period of time that exceeds a sum of a pulse duration of the beam of illumination light and the temporal delay.

2. The inspection system of claim 1, wherein the temporal delay exceeds a pulse duration of the beam of illumination light generated by the pulsed laser illumination source.

3. The inspection system of claim 2, wherein the temporal delay is less than a period between successive pulses of the illumination light generated by the pulsed laser illumination source.

4. The inspection system of claim 1, wherein the optical subsystem includes two parallel mirrors configured to spatially split the beam of illumination light into two half-beams, wherein one half-beam is spatially displaced and temporally delayed with respect to the other.

5. The inspection system of claim 1, wherein the optical subsystem includes at least one beam splitter and a mirror configured to generate two or more secondary illumination beams from the beam of illumination light, wherein each of the secondary illumination beams are temporally delayed with respect to any other of the secondary illumination beams.

6. The inspection system of claim 1, wherein the optical subsystem includes a parallel beam plate configured to spatially split the beam of illumination light into four half-beams of approximately equal intensity, wherein each of the four half-beams is temporally delayed with respect to at least one of the others.

7. The inspection system of claim 6, wherein the parallel beam plate is further configured to emit a first and a second of the four half-beams from a first surface of the parallel beam plate and third and a fourth of the four half-beams from a second surface of the parallel beam plate.

8. The inspection system of claim 1, wherein the detector is a time-delay integration (TDI) detector.

9. An inspection system comprising:
an illumination source configured to generate a pulsed beam of illumination light;
an optical subsystem that receives the pulsed beam of illumination light and splits the pulsed beam of illumination light into two or more secondary beams of illumination light, wherein the optical subsystem introduces a spatial separation among the two or more secondary beams of illumination light as the two or more secondary beams illuminate a surface of a specimen under inspection; and
a time-delay integration (TDI) detector operable to receive a first amount of light collected from the surface of the specimen illuminated by a first of the two or more secondary beams of illumination light, receive a second amount of light collected from the surface of the specimen illuminated by a second of the two or more secondary beams of illumination light, and generate an output value based on a time-delay integration of the first and second amounts of collected light, wherein an integration time associated with the time-delay integration is at least five times longer than a time between successive pulses.

10. The inspection system of claim 9, wherein the optical subsystem includes two parallel mirrors configured to spatially split the beam of illumination light into two half-beams, wherein one half-beam is spatially displaced with respect to the other.

11. The inspection system of claim 9, wherein the optical subsystem includes at least one beam splitter and a mirror configured to generate two or more secondary illumination beams from the beam of illumination light, wherein each of the secondary illumination beams are spatially displaced with respect to any other of the secondary illumination beams.

12. The inspection system of claim 9, wherein the optical subsystem includes a parallel beam plate configured to spatially split the beam of illumination light into four half-beams of approximately equal intensity, wherein each of the four half-beams is spatially displaced with respect to at least one of the others.

13. The inspection system of claim 12, wherein the parallel beam plate is further configured to emit a first and a second of the four half-beams from a first surface of the parallel beam plate and third and a fourth of the four half-beams from a second surface of the parallel beam plate.

14. A method comprising:
generating a pulsed beam of illumination light;
splitting the pulsed beam of illumination light into two or more secondary beams of illumination light with a temporal delay among the two or more secondary beams of illumination light as the two or more secondary beams illuminate a surface of a specimen under inspection;
receiving a first amount of light collected from the surface of the specimen illuminated by a first of the two or more secondary beams of illumination light;
receiving a second amount of light collected from the surface of the specimen illuminated by a second of the two or more secondary beams of illumination light; and
generating an output value based on an integration of the first and second amounts of collected light over a period of time that is at least five times longer than a time between successive pulses of the pulsed beam of illumination light.

15. The method of claim 14, wherein the splitting the pulsed beam of illumination light into the two or more secondary beams of illumination light involves spatially splitting the beam of illumination light into two half-beams, wherein one half-beam is temporally delayed with respect to the other.

16. The method of claim 14, wherein the temporal delay exceeds a pulse duration of the pulsed beam of illumination light.

17. The method of claim 16, wherein the temporal delay is shorter than a period between successive pulses of the pulsed beam of illumination light.

18. A method comprising:
generating a pulsed beam of illumination light;
splitting the pulsed beam of illumination light into two or more secondary beams of illumination light, wherein each area of a surface of a specimen illuminated by each of the two or more secondary beams of illumination light is spatially separated;
receiving a first amount of light collected from the surface of the specimen illuminated by a first of the two or more secondary beams of illumination light;
receiving a second amount of light collected from the surface of the specimen illuminated by a second of the two or more secondary beams of illumination light; and
generating an output value based on a time-delay integration of the first and second amounts of collected light, wherein an integration time associated with the time-delay integration is at least five times longer than a time between successive pulses.

19. The method of claim 18, wherein the splitting the beam of illumination light into the two or more secondary beams of illumination light involves a diffractive optical element.

* * * * *